United States Patent [19]
Khan et al.

[11] Patent Number: 5,656,296
[45] Date of Patent: Aug. 12, 1997

[54] DUAL CONTROL SUSTAINED RELEASE DRUG DELIVERY SYSTEMS AND METHODS FOR PREPARING SAME

[75] Inventors: Sadath U. Khan, Randolph; Phyllis Ying, Morristown; Russell U. Nesbitt, Somerville; Mahdi B. Fawzi, Flanders; Jay Weiss, East Brunswick, all of N.J.

[73] Assignee: Warner-Lambert Company, Morris Plains, N.J.

[21] Appl. No.: 476,490

[22] Filed: Jun. 7, 1995

Related U.S. Application Data

[63] Continuation of Ser. No. 275,198, Jul. 14, 1994, abandoned, which is a continuation of Ser. No. 875,846, Apr. 29, 1992, abandoned.

[51] Int. Cl.$^6$ .................................................. A61K 9/24
[52] U.S. Cl. ...................... 424/473; 424/472; 424/474; 424/481; 424/482; 424/440
[58] Field of Search ........................... 424/473, 472, 424/474, 481, 482, 440

[56] References Cited

U.S. PATENT DOCUMENTS

| | | | |
|---|---|---|---|
| 4,756,911 | 7/1988 | Drost | 424/468 |
| 4,789,549 | 12/1988 | Khan | 424/480 |
| 4,797,288 | 1/1989 | Sharma | 424/476 |
| 4,816,264 | 3/1989 | Phillips | 424/468 |
| 4,851,233 | 7/1989 | Khan | 424/480 |
| 4,892,742 | 1/1990 | Shah | 424/480 |
| 4,983,401 | 1/1991 | Eichez | 424/473 |
| 5,032,406 | 7/1991 | Dansereau | 424/472 |
| 5,068,110 | 11/1991 | Fawzi | 424/461 |

*Primary Examiner*—D. Gabrielle Phelan
*Attorney, Agent, or Firm*—Michael J. Atkins

[57] ABSTRACT

The present invention pertains to a dual control sustained release drug delivery system which comprises a core and a porous coating layer over the core, wherein the coated core comprises (A) a core comprising in percentages by weight of the core composition (a) a medicament present in an amount from about 60% to about 90%; (b) an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof, present in an amount from about 5% to about 40%; and (B) a porous coating layer over the core comprising in percentages by weight of the coating layer composition (a) a pH-independent water-insoluble polymer present in an amount from about 40% to about 80%; and (b) a water-soluble film forming polymer present in an amount from about 20% to about 60%.

15 Claims, 1 Drawing Sheet

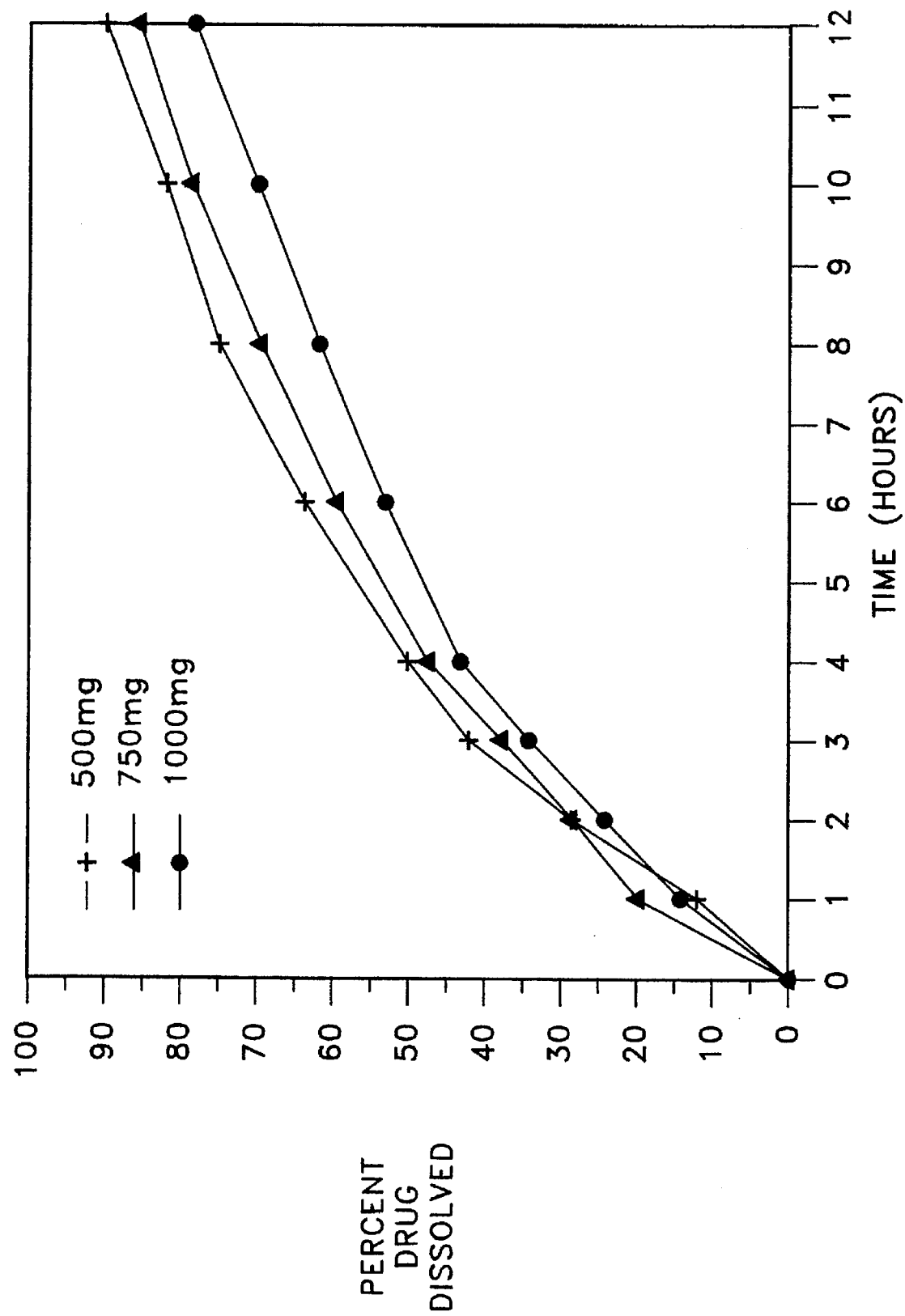

DUAL CONTROL SUSTAINED RELEASE DRUG DELIVERY SYSTEMS AND METHODS FOR PREPARING SAME

This is a continuation of prior application Ser. No. 08/275,198 as originally filed on Jul. 14, 1994, now abandoned which was a continuation of U.S. Ser. No. 07/875,846 filed Apr. 29, 1992, now abandoned.

BACKGROUND OF THE INVENTION

1. Field of the Invention

This invention pertains to dual control sustained release drug delivery systems. The novel drug delivery systems contain a core comprising a medicament and a waxy material and a coating layer over the core comprising a pH-independent water-insoluble polymer and a water-soluble polymer. Therapeutically effective amounts of the drug delivery systems may be utilized in a wide variety of pharmaceutically acceptable carriers to prepare medicated sustained release compositions. This invention also relates to methods for preparing these drug delivery systems and the medicated sustained release compositions in which they may be used.

2. Description of the Background

Sustained release compositions for the sequential or timed release of medicaments are well known in the art. Generally such compositions contain medicament particles, normally administered in divided doses two or more times daily, mixed with or covered by a coating material which is resistant to degradation or disintegration in the stomach and/or in the intestine for a selected period of time. Release of the medicament may occur by leaching, erosion, rupture, diffusion or similar actions, depending upon the nature and thickness of the coating material.

A frequently encountered problem in the field of sustained release compositions is that many water-miscible drugs have a tendency to be dumped or surged into the body during the first hour or two after an oral dosage form is ingested. This problem is particularly acute when the sustained release compositions are administered with food.

U.S. Pat. No. 4,789,549, issued to Khan et al. and assigned to Warner-Lambert Company, discloses a sustained release composition comprising a medicament in a water-soluble polymer matrix coated with a semi-permeable membrane coating layer consisting of hydroxypropyl cellulose and cellulose acetate phthalate with polyoxypropylene polyoxyethylene block copolymer and acetylated monoglycerides. The water-soluble polymer matrix is preferably hydroxypropyl methylcellulose.

U.S. Pat. No. 4,816,264, issued to Phillips et al. and assigned to Warner-Lambert Company, discloses a sustained release drug delivery system containing a core comprising a medicament and a cellulosic gelling polymer such as hydroxyethyl cellulose coated with a semi-permeable membrane coating layer comprising a water-soluble cellulosic polymer such as hydroxypropyl cellulose and a water-insoluble acrylic polymer such as Eudragit E30D.

U.S. Pat. No. 4,851,233, issued to Khan et al. and assigned to Warner-Lambert Company, discloses a compressed table binder system consisting essentially of procainamide hydrochloride or sodium meclofenamate, type "H" hydroxyethyl cellulose, and microcrystalline cellulose coated with hydroxyethyl cellulose.

While the above sustained release compositions provide some degree of improved sustained release activity, none of the above compositions are entirely satisfactory. All of the above sustained release compositions have a tendency to rapidly release water-miscible drugs into the body when the sustained release compositions are administered with food. Thus it would be advantageous to prepare a sustained release composition having release properties which are unaffected by the consumption of food. The present invention provides such improved sustained release drug delivery systems without the disadvantages characteristic of previously known products. The present invention also provides methods for preparing these improved sustained release drug delivery systems and the medicated sustained release compositions in which they may be employed.

SUMMARY OF THE INVENTION

The present invention pertains to a dual control sustained release drug delivery system which comprises a core and a porous coating layer over the core, wherein the coated core comprises:

(A) a core comprising in percentages by weight of the core composition:
  (a) a medicament present in an amount from about 60% to about 90%;
  (b) an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof, present in an amount from about 5% to about 40%; and (B) a porous coating layer over the core comprising in percentages by weight of the coating layer composition:
  (a) a pH-independent water-insoluble polymer present in an amount from about 40% to about 80%; and
  (b) a water-soluble film forming polymer present in an amount from about 20% to about 60%.

BRIEF DESCRIPTION OF THE FIGURE

FIG. 1 is a graph showing the in vitro dissolution profile of a procainamide hydrochloride prolonged release tablet over a 12 hour period prepared according to the present invention.

DETAILED DESCRIPTION OF THE INVENTION

The present invention pertains to a sustained release drug delivery systems having a dual control mechanism. The drug delivery system contains a core comprising a medicament and a waxy material and a porous coating layer over the core comprising a pH-independent water-insoluble polymer and a water-soluble film forming polymer. Applicants have found that conventional sustained release compositions containing a water-soluble polymer matrix in the core have a tendency to either dump or delay the release of a medicament when administered with a high fat meal. Applicants have discovered that sustained release compositions containing the combination of a core having a medicament and a waxy material and a semi-permeable coating layer are essentially unaffected by food consumption. The dual control mechanism is achieved by employing a fatty acid or waxy material in the core and a specific combination of polymeric materials in the porous coating layer. The improved dual control sustained release drug delivery systems prolong the release of medicaments for up to 12 hours or more.

The dual control sustained release drug delivery systems may be utilized in a wide variety of pharmaceutically acceptable carriers and confectionery bulking agents to prepare medicated sustained release compositions. This invention also relates to methods for preparing these dual control sustained release drug delivery systems and the medicated sustained release compositions in which they may be employed.

As set out above, the dual control sustained release drug delivery systems contain a core comprising a medicament and an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof.

The medicaments (drugs, pharmaceuticals) present in the core of the drug delivery system of the present invention may be selected from a wide variety of water-soluble and water-insoluble drugs and their acid addition or metallic salts. Both organic and inorganic salts may be used provided the drug maintains its medicament value. Exemplary acid addition salts include hydrochloride, hydrobromide, orthophosphate, benzoate, maleate, tartrate, succinate, citrate, salicylate, sulfate and acetate. Exemplary metallic salts include sodium, potassium, calcium, and magnesium.

The medicament may be selected from a wide range of therapeutic agents and mixtures of therapeutic agents which may be administered in sustained release or prolonged action form. Nonlimiting illustrative categories and specific examples of such medicaments include:

(a) Analgesics, such as acetylsalicylic acid, acetaminophen, ibuprofen, phenacetin, phenylbutazone, salicylamide, sodium salicylate, and meclofenamic acid;

(b) Anthelmintics, such as dithiazanine iodide and gardona;

(c) Antiasmatics, such as aminophylline, metaproterenol, epinephrine, theophylline, and oxtriphylline;

(d) Antiarrhythmics, such as procainamide hydrochloride and pirminol;

(e) Anticholesterolemic and antilipid agents, such as gemfibrozil, HMG reductase inhibitors, and ACAT inhibitors;

(f) Antiemetics, such as prochloroperazine dimaleate;

(g) Antiepileptic drugs, such as sodium phenytoin;

(h) Antihistamines, such as chlorpheniramine maleate, brompheniramine maleate, phenindamine tartrate, pyrilamine maleate, methapyrilene fumarate, doxylamine succinate, phenyltoloxamine citrate, diphenylhydramine hydrochloride, promethazine, terfenedine and triprolidine;

(i) Antihypertensives, such as methyldopa;

(j) Anti-inflammatory agents, such as isoxicam, meclofenamic acid, sodium meclofenamate, and naproxen;

(k) Antinauseants, such as dimenhydrinate and meclizine;

(l) Antipyretics, such as N-acetyl-p-aminophenol;

(m) Antitussives, such as dextromethorphan, dextromethorphan hydrobromide, noscapine, carbetapentane citrate, chlophedianol hydrochloride, codeine and diphenhydramine hydrochloride;

(n) Anxiety agents, such as buspirone hydrochloride and N-methylglucamine;

(o) Appetite suppressants, such as phenylpropanolamine hydrochloride and caffeine;

(p) Cathartics, such as castor oil;

(q) Central nervous system stimulants, such as nicotine and caffeine;

(r) Cardiovascular preparations, such as angiotensin converting enzyme inhibitors (ACE inhibitors), including enalapril maleate and catopril; calcium channel blockers, including verapamil hydrochloride;

(s) Cognition activators such as tactine;

(t) Decongestants, such as phenylephrine hydrochloride, phenylpropanolamine hydrochloride, pseudoephedrine hydrochloride, pseudoephedrine hydrobromide, pseudoephedrine sulfate and ephedrine;

(u) Expectorants, such as guaifenesin and glycerol guaiacolate;

(v) Laxatives, such as phenolphthalein, danthron, pamabrom and bisocadyl;

(w) Nutritional supplements, including vitamins and minerals, such as ascorbic acid, niacin, pantothenic acid, vitamin B6, thiamine hydrochloride, riboflavin, potassium iodide, potassium chloride, cupric sulfate and ferrous sulfate; and (x) Various alkaloids, such as codeine phosphate, codeine sulfate and morphine.

Preferred drugs to be employed include sparingly soluble drugs such as sodium meclofenamate, meclofenamic acid, methyldopa, sodium phenytoin, and the like, and freely soluble drugs such as diphenhydramine hydrochloride, pseudoephedrine hydrochloride, procainamide hydrochloride, and oxtriphylline. In a preferred embodiment, the medicament is selected from the group consisting of sodium meclofenamate and procainamide hydrochloride. In a more preferred embodiment, the medicament is procainamide hydrochloride.

The medicament of the present invention may be used in many distinct physical forms well known in the pharmaceutical art to provide an initial dosage of the medicament and/or a further time-release form of the medicament. Without being limited thereto, such physical forms include free forms and encapsulated forms, and mixtures thereof.

The amount of medicament drug or its acid addition salt used in the present invention may vary depending upon the therapeutic dosage recommended or permitted for the particular medicament. In general, the amount of medicament present is the ordinary dosage required to obtain the desired result. Such dosages are known to the skilled practitioner in the medical arts and are not a part of the present invention. In a preferred embodiment, the medicament in the core of the drug delivery system is present in an amount from about 60% to about 90%, preferably from about 70% to about 90%, and more preferably from about 75% to about 85%, by weight of the core composition.

The edible material present in the core of the drug delivery system of the present invention is a material which has a melting point in the range from about 25° C. to about 100° C., preferably from about 35° C. to about 100° C., and more preferably from about 45° C. to about 100° C. The melting point of the edible material should be within the recited range because the sustained release properties of the final drug delivery system will be greatly affected by the fat or wax constituent.

The edible materials useful in the core are selected from the group consisting of fatty acids, natural waxes, synthetic waxes, and the like, and mixtures thereof. Fatty acids are carboxylic acids derived from or contained in an animal or vegetable fat or oil. Fatty acids are composed of a chain of alkyl groups containing from 4 to 22 carbon atoms and are characterized by a terminal carboxyl group. Waxes are low-melting organic mixtures or compounds having a high molecular weight, are solid at room temperature and generally are similar in composition to fats and oils except that waxes contain no glycerides. Waxes may be hydrocarbons or esters of fatty acids and alcohols. Fatty acids and waxes are both classified as lipids.

The fatty acids useful in the present invention are acids which have an iodine value from about 1 to about 10. The iodine value is a means of determining the degree of unsaturation in a fat or oil. The measurement of iodine values is determined by known titrating methods and is reported in terms of centigrams of iodine absorbed per gram of fat or oil sample titrated. (See "Bailey's Industrial Oil and Fat Products," Vol. 2, 4th Ed., Swern, Daniel ed., pp. 436–438 (1982)). Hence the fatty acids useful in the present invention have an iodine value from about 1 centigram to about 10 centigrams.

Fatty acids useful in the present invention are selected from the group consisting of hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil, hydrogenated castor oil, and the like, and mixtures thereof. Other fatty acids include, for example, decenoic acid, docosanoic acid, stearic acid, palmitic acid, lauric acid, myristic acid, and the like, and mixtures thereof. The preferred fatty acids are selected from the group consisting of hydrogenated palm oil, hydrogenated castor oil, hydrogenated cottonseed oil, stearic acid, palmitic acid, and mixtures thereof. The most preferred fatty acid is stearic acid.

Waxes useful in the present invention include natural waxes, such as animal waxes, vegetable waxes, and petroleum waxes (i.e., paraffin waxes, microcrystalline waxes, petrolatum waxes, mineral waxes), and synthetic waxes which are edible and have a melting point within the range from about 25° C. to about 100° C. Specific examples of useful waxes are spermaceti wax, carnauba wax, Japan wax, bayberry wax, flax wax, beeswax, Chinese wax, shellac wax, lanolin wax, sugarcane wax, candelilla wax, paraffin wax, microcrystalline wax, petrolatum wax, carbowax, and the like, and mixtures thereof. Mixtures of these waxes with the fatty acids set out above may also be used. The preferred waxes are selected from the group consisting of carnauba wax, bees wax, glyceryl tristearate, glyceryl monostearate, paraffin wax, microcrystalline wax, glyceryl distearate, and mixtures thereof. The most preferred waxes are carnauba wax, bees wax, glyceryl tristearate, glyceryl monostearate, and paraffin wax.

The wax may also be an ester of a fatty acid having from about 12 to about 31 carbon atoms and a fatty alcohol having from about 12 to about 31 carbon atoms, the ester having a carbon atom content from about 24 to about 62 carbon atoms. Examples of such fatty, acid esters are myricyl palmitate, ceryl palmitate, ceryl cerotate, myricyl melissate, stearyl palmitate, stearyl myristate, lauryl laurate, and the like, and mixtures thereof. The preferred fatty acid esters are selected from the group consisting of stearyl palmitate, stearyl myristate, and mixtures thereof.

The wax may also be a monoglyceryl ester, diglyceryl ester, or triglyceryl ester (glycerides) which is an ester formed from a fatty acid having from about 10 to about 22 carbon atoms and glycerol, wherein one or more of the hydroxyl groups of glycerol is substituted by a fatty acid. Examples of useful glycerides include glyceryl monostearate, glyceryl distearate, glyceryl tristearate, glyceryl dipalmitate, glyceryl tripalmitate, glyceryl monopalmitate, glyceryl dilaurate, glyceryl trilaurate, glyceryl monolaurate, glyceryl didocosanoate, glyceryl tridocosanoate, glyceryl monodocosanoate, glyceryl monocaproate, glyceryl dicaproate, glyceryl tricaproate, glyceryl monomyristate, glyceryl dimyristate, glyceryl trimyristate, glyceryl monodecenoate, glyceryl didecenoate, glyceryl tridecenoate, and the like, and mixtures thereof. The preferred glycerides are selected from the group consisting of glyceryl monostearate, glyceryl distearate, glyceryl tristearate, and mixtures thereof.

In a preferred embodiment, the edible material is selected from the group consisting of carnauba wax, hydrogenated vegetable oils, and stearic acid. More preferably, the edible material is carnauba wax.

The amount of edible material used in the core may vary depending upon the medicament employed and the degree of sustained release desired. In general, the fatty acid or waxy edible material will be present in the core in an amount from about 5% to about 40%, preferably from about 5% to about 30%, and more preferably from about 5% to about 15%, by weight of the core composition.

The core of the drug delivery system of the present invention may also contain conventional excipients and additives which function to facilitate processing or storage. Thus coloring agents, flavoring agents, perfumes, sweetening agents, surface active agents, lubricants, softeners, glidants, stabilizing agents, and the like, and mixtures thereof, may be employed.

As set out above, the cores in the drug delivery systems are coated with a porous coating layer comprising a pH-independent water-insoluble polymer present and a water-soluble film forming polymer.

The pH-independent water-insoluble polymers in the coating layer of the drug delivery system of the present invention are preferably acrylic polymers. Suitable water-insoluble polymers in the present invention include aqueous acrylic resin dispersions such as polyacrylamide, polyacryldextran, polyalkyl cyanoacrylate, polymethyl methacrylate, methacrylic resin copolymer, and the like, and mixtures thereof. Preferred resins are the Eudragits™ (methacrylic resin copolymer), made by Rohm Pharma. Eudragit NE30D™ is highly preferred.

The amount of pH-independent water-insoluble polymer used in the present invention may vary depending upon the medicament employed and the degree of sustained release desired. The pH-independent water-insoluble polymer in the coating layer is preferably present in an amount from about 40% to about 80%, more preferably from about 50% to about 75%, and most preferably from about 55% to about 70%, by weight of the coating layer composition.

The water-soluble film forming polymers in the coating layer of the drug delivery system of the present invention include cellulose derivatives such as hydroxypropylcellulose, hydroxypropyl-methylcellulose, hydroxypropylmethylcellulose phthalate, sodium carboxymethylcellulose, and the like, and mixtures thereof. In a preferred embodiment, the film forming polymer is hydroxypropylcellulose.

The amount of water-soluble film forming polymer used in the present invention may vary depending upon the medicament employed and the degree of sustained release desired. The water-soluble film forming polymer in the coating layer is preferably present in an amount from about 20% to about 60%, more preferably from about 25% to about 50%, and most preferably from about 30% to about 45%, by weight of the coating layer composition.

The coating layer of the drug delivery system of the present invention may also contain conventional excipients and additives which function to facilitate processing or storage. Thus antifoam agents, fillers, plasticizing agents, coloring agents, flavoring agents, perfumes, sweetening agents, surface active agents, lubricants, stabilizing agents, anti-tacking agents, and the like, and mixtures thereof, may be employed.

The weight ratio of core composition to coating layer composition is the ratio containing sufficient coating layer to prevent potential premature release of the medicament from the core without forming a composition so large as to be therapeutically unsuitable for use. In general, the weight ratio of core composition to coating layer composition is from about 94:6 to about 98:2, preferably from about 95:5 to about 98:2, and more preferably from about 96:4 to about 98:2, respectively.

The coated cores may also be agglomerates of coated cores which may contain one or more core gathered into a cluster under a single coating layer. The terms "coated cores" and "agglomerates of coated cores" are used interchangeably herein.

The present invention is also directed at methods for preparing the dual control sustained release drug delivery systems. In general, the drug delivery systems are prepared by first melting the fatty acid or waxy edible material and then admixing the medicament and traditional additives such as softeners into the melted core. The melted core is then cooled, congealed, and milled to the desired particle size. Additives such as glidants and lubricants may then be admixed with the milled mixture. The mixture is then compressed into tablet cores and is ready to be coated with the porous coating layer.

A suspension of the porous coating layer is then prepared by admixing the pH-independent water-insoluble polymer and the water-soluble film forming polymer in water with traditional additives such as a softener, an antifoaming agent, and an anti-tacking agent. The coating layer suspension is sprayed onto the tablets until the weight increase in the tablets is the range from about 4% to about 8%. A color coat may optionally be applied to the coated tablets to improve the aesthetics of the tablets.

The drug delivery systems of the present invention may be admixed, compressed, and spray coated using standard techniques and equipment known to those skilled in the art. The exact conditions for forming and compressing tablet cores and spray coating the cores will vary with the particular apparatus selected and are readily determined by those skilled in the art without the need for undue experimentation. Tablet compressing and pan coating are well known in the arts and therefore the selection of the specific apparatus will be apparent to the artisan.

In a specific embodiment, the present invention is directed at a method for preparing a dual control sustained release drug delivery system which comprises a core and a porous coating layer over the core, which comprises the steps of:

(1) providing the following ingredients:
 (A) a core comprising in percentages by weight of the core composition:
  (a) a medicament present in an amount from about 60% to about 90%;
  (b) an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof, present in an amount from about 5% to about 40%; and (B) a porous coating layer over the core comprising in percentages by weight of the coating layer composition:
  (a) a pH-independent water-insoluble polymer present in an amount from about 40% to about 80%; and
  (b) a water-soluble film forming polymer present in an amount from about 20% to about 60%;

(2) melting the edible material from step (1)(A)(b) and admixing the medicament from step (1)(A)(a) to form a molten mixture;

(3) cooling and milling the mixture from step (2) and compressing milled mixture to form tablet cores;

(4) admixing the ingredients from step (1)(B) in water to form a porous coating layer suspension; and (5) coating the tablet cores from step (3) with the coating layer suspension from step (4) to form the dual control sustained release drug delivery system.

Once prepared, the coated core compositions may be stored for future use or may be formulated with conventional additives such as pharmaceutically acceptable carriers and confectionery bulking agents to prepare a wide variety of medicated sustained release compositions to suit particular applications.

An important aspect of the present invention includes a hard or soft confectionery composition incorporating the inventive drug delivery systems and a method for preparing the hard or soft confections. In this form of the invention, the medicated sustained release compositions includes the coated cores and a pharmaceutically acceptable carrier such as a confectionery bulking agent, and various additives. The confectionery may be in the form of a lozenge, tablet, toffee, nougat, suspension, chewy candy, and the like. The pharmaceutically acceptable carriers may be prepared from a wide range of materials. Without being limited thereto, such materials include diluents, binders and adhesives, lubricants, disintegrants, coloring agents, bulking agents, flavoring agents, sweetening agents and miscellaneous materials such as buffers and adsorbents in order to prepare a particular medicated confection.

The preparation of confectionery formulations is historically well known and has changed little through the years. Confectionery items have been classified as either "hard" confectionery or "soft" confectionery. The medicated compositions of the present invention can be incorporated into confectionery compositions by admixing the inventive compositions into conventional hard and soft confections.

As used herein, the term confectionery material means a product containing a bulking agent selected from a wide variety of materials such as sugar, corn syrup, and the like, and in the case of sugarless bulking agents, sugar alcohols such as sorbitol and mannitol and the like, and mixtures thereof. Confectionery material may include such exemplary substances as lozenges, tablets, toffee, nougat, suspensions, chewy candy, chewing gum and the like. The bulking agent is present in a quantity sufficient to bring the total amount of confectionery composition to 100%.

Lozenges are flavored medicated dosage forms intended to be sucked and held in the mouth. Lozenges may be in the form of various shapes such as flat, circular, octagonal and biconvex forms. The lozenge bases are generally in two forms: hard, boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and the cooking continued until a final temperature of 145° C. to 156° C. is achieved. The batch is then cooled and worked as a plastic-like mass to incorporate additives such as flavoring agents, coloring agents and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavor agents, coloring agents and the like.

In vacuum cookers, the carbohydrate bulking agent is boiled at a temperature from about 125° C. to about 132° C., vacuum is applied and additional water is boiled off without extra heating. When cooking is complete, the mass is a semi-solid and has a plastic-like consistency. At this point, flavoring agents, coloring agents, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from about 4 to about 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieherman, Pharmaceutical Dosage Forms: Tablets, Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agents, coloring agents, preservatives, medicaments, mixtures thereof and the like may be added thereafter also under agitation. A general discussion of the composition and preparation of nougat confections may be found in B. W. Minifie, Chocolate, Cocoa and Confectionery: Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes.

The novel medicated sustained release compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as benzoic acid, sorbic acid, methyl paraben, and propyl paraben. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate which may be present in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacis, and microcrystalline cellulose which may be present in amounts up to about 20%, and preferably from about 1% to about 15%, by weight of the suspension;

(d) antifoaming agents such as dimethyl polysiloxane which may be present in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These coloring agents are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) vehicles such as propylene glycol, polyethylene glycol, edible oils such as animal, vegetable and mineral oils, and the like may be used to solubilize the flavoring agents. In general, vehicles may be used in amounts up to about 10%, and preferably from about 2% to about 5%, by weight of the suspension.

The pharmaceutical suspensions of the present invention may be prepared as follows:

(A) admix the thickener with the vehicle heated to a temperature from about 40° C. to about 95° C., preferably from about 40° C. to about 70° C., to form a dispersion if the thickener is soluble in the vehicle or a solution if the thickener is soluble in the soluble;

(B) admix the sweetening agent with the vehicle to form a solution;

(C) admix the sustained release composition with the thickener-vehicle admixture to form a uniform thickener-sustained release composition;

(D) combine the sweetener solution with the thickener-sustained release composition and mix until uniform; and (E) admix the optional adjunct materials such as coloring agents, flavoring agents, decolorants, solubilizing agents, antifoaming agents, buffers and additional vehicle with the mixture of step (D) to form the suspension.

To achieve acceptable stability and quality as well as good taste and mouth feel in a sustained release formulation several considerations are important. These considerations include the amount of active substance per tablet, the flavoring agent employed, the degree of compressibility of the tablet and the organoleptic properties of the pharmaceutical composition.

Medicated candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The drug delivery systems of the present invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and tablet forms of confectionery may be found in H. A. Lieherman and L. Lachman, *Pharmaceutical Dosage Forms: Tablets* Volume 1, Marcel Dekker, Inc., New York, N.Y. at pages 289 to 466, which disclosure is incorporated herein by reference.

In accordance with this invention, therapeutically effective amounts of the drug delivery system of the present invention may be admixed into the hard and soft confections. These amounts are readily determined by those skilled in the art without the need for undue experimentation. The exact amount of the drug delivery system employed in the hard and soft confections will vary with the particular medicament selected. In a preferred embodiment, the drug delivery system is present in the hard and soft confection compositions in percentages by weight in an amount from about 5% to about 50%, more preferably from about 10% to about 40%, and most preferably, in an amount from about 10% to about 30%. The pharmaceutically acceptable carrier and optional additives are present in a quantity sufficient to bring the total amount of hard and soft confection composition to 100%.

The present invention extends to methods of making the improved medicated hard and soft confection compositions. The drug delivery systems may be incorporated into otherwise conventional hard or soft confection compositions using standard techniques and equipment known to those skilled in the art.

The apparatus useful in accordance with the present invention comprises cooking and mixing apparatus well known in the confectionery manufacturing arts, and therefore the selection of the specific apparatus will be apparent to the artisan.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLE

This Example demonstrates the preparation of dual control sustained release drug delivery systems according to the present invention.

Drug delivery systems were prepared according to the present invention having the compositions set out below in Table 1.

TABLE 1

Procainamide Hydrochloride
Inventive Prolonged Release Tablet Formulations

|  | 500 mg | 750 mg | 1000 mg |
| --- | --- | --- | --- |
| Tablet Core |  |  |  |
| Procainamide Hydrochloride USP | 79.42% | 80.91% | 79.77% |
| Carnauba Wax FCC, | 11.12% | 11.33% | 11.16% |
| Softening agent | 1.11% | 1.13% | 1.12% |
| Glidant | 0.16% | 0.16% | 0.16% |
| Lubricant | 0.32% | 0.32% | 0.32% |
| Porous Coating Layer |  |  |  |
| Hydroxypropyl Cellulose NF | 0.66% | 0.49% | 0.67% |
| Eudragit NE30D | 2.48% | 1.484 | 2.01% |
| Anti-foaming agent | 0.07% | 0.054 | 0.07% |
| Softening agent | 0.33% | 0.25% | 0.34% |
| Anti-tacking agent | 1.98% | 1.48% | 2.01% |
| Purified Water USP | q.s | q.s | q.s |
| Color Coat |  |  |  |
| Opadry | 2.26% | 2.31% | 2.28% |
| Anti-foaming agent | 0.04% | 0.04% | 0.04% |
| Purified Water USP | q.s | q.s | q.s |
| Candelilla Wax | 0.05% | 0.05% | 0.05% |

A control drug delivery composition was prepared having the composition set out below in Table 2.

TABLE 2

Procainamide Hydrochloride
Control Tablet Formulations

|  | 500 mg | 750 mg | 1000 mg |
| --- | --- | --- | --- |
| Tablet Core |  |  |  |
| Procainamide Hydrochloride USP | 65.27% | 83.80% | 83.82% |
| Carnauba Wax FCC, | 11.15% | 11.15% | 11.15% |
| Softening agent | 1.11% | 1.11% | 1.11% |
| Filler | 18.51 | — | — |
| Glidant | 0.22% | 0.23% | 0.23% |
| Lubricant | 0.34% | 0.34% | 0.34% |
| Color Coat |  |  |  |
| Opadry | 2.86% | 2.87% | 2.90% |
| Anti-foaming agent | 0.04% | 0.04% | 0.04% |
| Purified Water USP | — | — | — |
| Flavoring agent | <0.01% | <0.01% | <0.01% |

TABLE 2-continued

Procainamide Hydrochloride
Control Tablet Formulations

|  | 500 mg | 750 mg | 1000 mg |
| --- | --- | --- | --- |
| Polishing agent | 0.49% | 0.44% | 0.42% |
| Purified Water USP | — | — | — |

The dissolution profiles of the inventive drug delivery system set out in Table 1 and the control composition set out in Table 2 were then determined in vitro for one hour in 0.1N hydrochloric acid, then for 11 hours at pH 7.5 in phosphate buffer. The amount of drug dissolved was determined by ultraviolet absorbance analysis spectrophotometrically. FIG. 1 is a graph showing the in vitro percent drug dissolved versus time of the procainamide hydrochloride prolonged release tablets prepared according to the present invention over a 12 hour period.

Table 3 shows the mean steady-state pharmacokinetic parameters for the prolonged release of the inventive 500 mg procainamide hydrochloride tablets and a 500 mg control tablet. In Table 3, AUC is the bioavailability of the drug as determined by the plasma concentration percentage area under the curve, $C_{max}$ is the maximum concentration of the drug observed in plasma (ug/ml), $t_{max}$ is the time of maximum plasma concentration of the drug (hours), $C_{min}$ is the minimum concentration of the drug observed in plasma (ug/ml), RSD is the relative standard deviation given in parentheses in relation to the mean value.

TABLE 3

Mean Steady-State Procainamide Hydrochloride
Pharmacokinetics Parameters for 500 mg Prolonged Release
and 500 mg (Control) Tablet Doses

|  | Mean Value (% RSD) | | Mean Ratio |
| --- | --- | --- | --- |
| Parameter | Invention | Control | Invention/Control |
| AUC | 22.6 (19.9) | 25.6 (20.8) | 0.88 |
| $C_{max}$ | 2.62 (17.3) | 2.75 (19.6) | 0.95 |
| $t_{max}$ | 3.6 (28) | 1.9 (29) | 1.89 |
| $C_{min}$ | 1.31 (26.9) | 1.52 (20.5) | 0.86 |

Table 3 shows that the drug delivery systems of the present invention have satisfactory release sustaining properties.

Table 4 shows the food effect on the pharmacokinetic parameters of the procainamide hydrochloride 500 mg prolonged release tablets of the present invention. In Table 4, AUC (0-tldc) is the plasma concentration area under the curve from time zero to the time of last detectable concentration, AUC (0-infinity) is the plasma concentration area under the curve from time zero to time infinity, and $t_{1/2}$ is the apparent elimination half-life (hours).

TABLE 4

Effect of Food on the Pharmacokinetic Parameters
of Procainamide Hydrochloride
500 mg Prolonged Release Tablets

| Parameter | Mean Value (% RSD) | | Mean Ratio |
| --- | --- | --- | --- |
| | Fasted | Fed | Fed/Fasted |
| AUC (0-tldc) | 9.5 (15.1) | 10.4 (10.9) | 1.09 |
| AUC (0-infinity) | 10.1 (13.5) | 11.0 (10.9) | 1.09 |
| $C_{max}$ | 0.99 (20.9) | 1.24 (24.4) | 1.25 |
| $t_{max}$ | 4.8 (25.3) | 5.7 (29.6) | 1.19 |
| $t_{1/2}$ | 4.6 (16.7) | 4.0 (19.9) | 0.87 |

Table 4 shows that the drug delivery systems of the present invention are not significantly affected by food consumption.

The invention being thus described, it will be obvious that the same may be varied in many ways. Such variations are not to be regarded as a departure from the spirit and scope of the invention and all such modifications are intended to be included within the scope of the following claims.

We claim:

1. A dual control sustained release drug delivery system where the release of drug is essentially unaffected by high-fat food consumption which comprises a core and a porous coating layer over the core, wherein the coated core comprises:
   (A) a core comprising in percentages by weight of the core composition:
      (a) a medicament present in an amount from about 60% to about 90%;
      (b) an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof, present in an amount from about 5% to about 40%; and
   (B) a porous coating layer over the core comprising in percentages by weight of the coating layer composition:
      (a) a pH-independent water-insoluble polymer selected from the group consisting of acrylic resin dispersions consisting of polyacrylamide, polyacryldextran, polyalkyl cyanoacrylate, polymethacrylate, methacrylic resin copolymer, and mixtures thereof present in an amount from about 40% to about 80%;
      (b) a water-soluble film forming polymer present in an amount from about 20% to about 60%.

2. The drug delivery system according to claim 1, wherein the medicament in the core is present in an amount from about 70% to about 90%%, by weight of the core composition.

3. The drug delivery system according to claim 1, wherein the medicament in the core is selected from the group consisting of procainamide hydrochloride and sodium meclofenamate.

4. The drug delivery system according to claim 3, wherein the medicament in the core is procainamide hydrochloride.

5. The drug delivery system according to claim 1, wherein the edible material in the core is present in an amount from about 5% to about 30%, by weight of the core composition.

6. The drug delivery system according to claim 1, wherein the edible material in the core is selected from the group consisting of carnauba wax, hydrogenated vegetable oils, and stearic acid.

7. The drug delivery system according to claim 6, wherein the edible material in the core is carnauba wax.

8. The drug delivery system according to claim 1, wherein the water-insoluble polymer in the coating layer is present in an amount from about 50% to about 75%, by weight of the coating layer composition.

9. The drug delivery system according to claim 1, wherein the water-insoluble polymer in the coating layer is methacrylic resin copolymer.

10. The drug delivery system according to claim 1, wherein the water-soluble film forming polymer in the coating layer is present in an amount from about 25% to about 50%, by weight of the coating layer composition.

11. The drug delivery system according to claim 1, wherein the water-soluble film forming polymer is a cellulose derivative selected from the group consisting of hydroxypropylcellulose, hydroxypropylmethylcellulose, hydroxypropylmethylcellulose phthalate, sodium carboxymethylcellulose, and mixtures thereof.

12. The drug delivery system according to claim 12, wherein the water-soluble film forming polymer is hydroxypropyl cellulose.

13. The drug delivery system according to claim 1, wherein the weight ratio of core composition to coating layer composition is from about 94:6 to about 98:2, respectively.

14. A method for preparing a dual control sustained release drug delivery system where the release of drug is essentially unaffected by high-fat food consumption which comprises a core and a porous coating layer over the core, which comprises the steps of:
   (1) providing the following ingredients:
      (A) a core comprising in percentages by weight of the core composition:
         (a) a medicament present in an amount from about 60% to about 90%;
         (b) an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof, present in an amount from about 5% to about 40%; and
      (B) a porous coating layer over the core comprising in percentages by weight of the coating layer composition:
         (a) a pH-independent water-insoluble polymer selected from the group consisting of acrylic resin dispersions consisting of polyacrylamide, polyacryldextran, polyalkyl cyanoacrylate, polymethacrylate, methacrylic resin copolymer, and mixtures thereof present in an amount from about 40% to about 80%;
         (b) a water-soluble film forming polymer present in an amount from about 20% to about 60%;
   (2) melting the edible material from step (1)(A)(b) and admixing the medicament from step (1)(A)(a) to form a molten mixture;
   (3) cooling and milling the mixture from step (2) and compressing milled mixture to form tablet cores;
   (4) admixing the ingredients from step (1)(B) in water to form a porous coating layer suspension; and
   (5) coating the tablet cores from step (3) with the coating layer suspension from step (4) to form the dual control sustained release drug delivery system.

15. A medicated sustained release composition which comprises a pharmaceutically acceptable carrier, and a therapeutically effective amount of a drug delivery system where the release of drug is essentially unaffected by high-fat food consumption which comprises a core and a coating layer over the core, wherein the coated core comprises:

(A) a core comprising in percentages by weight of the core composition:
 (a) a medicament present in an amount from about 60% to about 90%;
 (b) an edible material having a melting point from about 25° C. to about 100° C. selected from the group consisting of (i) fatty acids having an iodine value from about 1 to about 10, (ii) natural waxes, (iii) synthetic waxes, and (iv) mixtures thereof, present in an amount from about 5% to about 40%; and (B) a porous coating layer over the core comprising in percentages by weight of the coating layer composition:
 (a) a pH-independent water-insoluble polymer selected from the group consisting of acrylic resin dispersions consisting of polyacrylamide, polyacryldextran,
 (b) a water-soluble film forming polymer present in an amount from about 20% to about 60%.

* * * * *